(12) United States Patent
Lewis et al.

(10) Patent No.: US 8,802,023 B1
(45) Date of Patent: Aug. 12, 2014

(54) AUTOCLAVE DOOR APPARATUS FOR AN AUTOCLAVE FOR TREATING MEDICAL WASTE

(75) Inventors: Robert W. Lewis, Charlotte, NC (US); Timothy A. Barrett, Douglassville, PA (US)

(73) Assignee: OnSite Sterilization LLC, Pottstown, PA (US)

( * ) Notice: Subject to any disclaimer, the term of this patent is extended or adjusted under 35 U.S.C. 154(b) by 151 days.

(21) Appl. No.: 13/200,740

(22) Filed: Sep. 29, 2011

(51) Int. Cl.
*A61L 2/00* (2006.01)
*F16J 15/02* (2006.01)
*E05F 7/02* (2006.01)
*E06B 7/18* (2006.01)
*A61L 2/07* (2006.01)
*A61L 9/015* (2006.01)
*A61L 12/00* (2006.01)
*C12H 1/08* (2006.01)
*C12H 1/18* (2006.01)

(52) U.S. Cl.
CPC .... *A61L 2/00* (2013.01); *A61L 2/07* (2013.01); *A61L 9/015* (2013.01); *A61L 12/00* (2013.01); *C12H 1/08* (2013.01); *C12H 1/18* (2013.01)
USPC ........... 422/296; 422/292; 422/295; 422/300; 422/305; 277/628; 49/255; 49/477.1

(58) Field of Classification Search
CPC ............. A61L 2/00; A61L 2/07; A61L 9/015; A61L 12/00; C12H 1/08; C12H 1/18
USPC .................. 422/26, 292, 295–296, 300, 305; 277/628; 49/255, 477.1; 220/324; 161/7; 219/400
See application file for complete search history.

(56) References Cited

U.S. PATENT DOCUMENTS

| 3,093,449 | A | * | 6/1963 | Kotarski et al. | 422/112 |
| 3,385,655 | A | * | 5/1968 | Huston et al. | 422/295 |
| 4,335,075 | A | * | 6/1982 | Kackos | 422/112 |
| 2003/0095891 | A1 | * | 5/2003 | O'Neal | 422/26 |

* cited by examiner

*Primary Examiner* — Monzer R Chorbaji
(74) *Attorney, Agent, or Firm* — John F. A. Earley, III; Frank J. Bonini, Jr.; Harding, Earley, Follmer & Frailey, P.C.

(57) ABSTRACT

A steam autoclave (steam sterilization system) has a door for opening and closing an opening that defines the entrance to and exit from a steam sterilization chamber. The door may be latched and locked and pneumatically sealed when in a closed position. Preferably, the door has a convex portion that projects into the sterilization chamber when the door is in a closed position for aiding in providing an even distribution of steam throughout the sterilization chamber during operation of the steam autoclave.

17 Claims, 8 Drawing Sheets

AUTOCLAVE DOOR APPARATUS FOR AN AUTOCLAVE FOR TREATING MEDICAL WASTE

FIELD OF THE INVENTION

This invention relates to steam autoclaves for treating medical waste, and more particularly concerns an autoclave door apparatus having a door that may be manually opened and closed and that may be sealed and locked in a closed position using pneumatics, as well as an autoclave for treating medical waste equipped with such an autoclave door apparatus.

BACKGROUND OF THE INVENTION

In a typical autoclave for the treatment of medical waste (e.g., Regulated Medical Waste), at least one access door is provided and may be opened to gain access to the sterilization chamber of the autoclave to permit loading of untreated medical waste into the sterilization chamber where the untreated medical waste may be treated and to permit unloading of treated medical waste from the sterilization chamber after treatment. A horizontally oriented autoclave may have an access door at one of its ends or both of its ends. When untreated medical waste is being treated in such an autoclave, the access door/doors is/are closed to seal off the sterilization chamber of the autoclave. Accordingly, each door is designed to handle the high pressures reached in the sterilization chamber during the autoclave treatment. Each such door typically is very heavy, and must be closed tightly during the autoclave treatment process to maintain proper pressure inside the sterilization chamber during the autoclave treatment process, and preferably is lockable in the closed position to prevent opening of the door while the sterilization chamber is under pressure.

Typically, such access doors are operated either hydraulically or manually. Hydraulically operated doors use pressure from a hydraulic pump to rotate door, ring or other mechanisms which are fitted with wedges, to create pressure between a fixed seal and opposing sealing surface. A drawback related to the use of hydraulically operated doors is the potential for leaks of hydraulic fluids into the environment. Further, the pressure wedges wear and are difficult to renew.

Manually operated doors operate similarly to hydraulically operated doors by forcing wedging members against fixed members, but rely on the operator to bring them into position with the appropriate sealing force.

SUMMARY OF THE INVENTION

It is an object of the invention to provide a door for an autoclave for the treatment of medical waste that seals the sterilization chamber of the autoclave during an autoclave treatment process, but eliminates the potential for leaks of hydraulic fluids into the environment and the drawbacks associated with wearing and renewal of pressure wedges.

It is another object of the invention to provide a door for an autoclave for the treatment of medical waste that seals the sterilization chamber of the autoclave during an autoclave treatment process, but eliminates reliance on the autoclave operator to manually tighten the door sufficiently to maintain the optimum seal pressure throughout an autoclave treatment process.

These and other objects are provided by our invention which is set out below.

DETAILED DESCRIPTION

Figure 1:
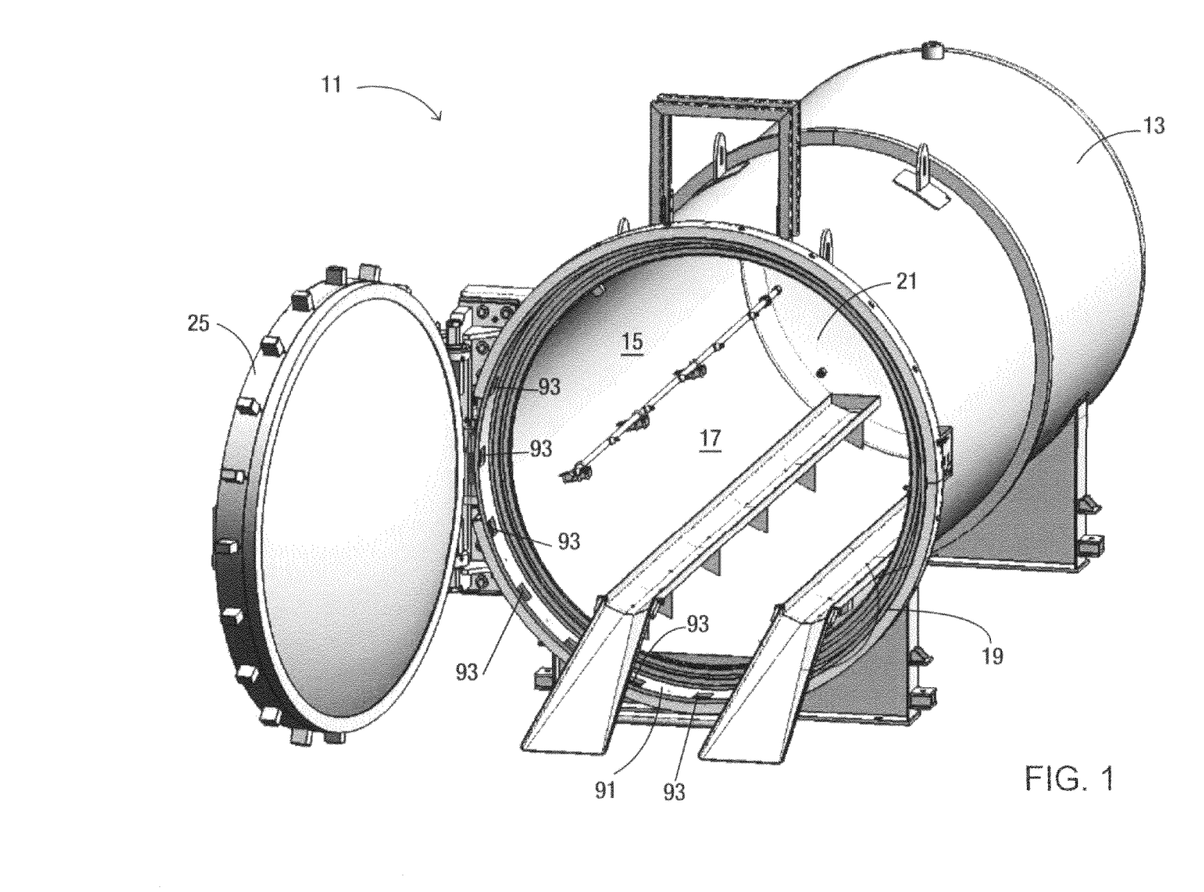
FIG. 1 is a view in perspective of a steam autoclave (steam sterilization system) 11 constructed in accordance with the invention.

Turning to the drawing, there is shown our steam autoclave (steam sterilization system) 11 for treating (e.g., sterilizing) material and objects such as medical waste (e.g., Regulated Medical Waste). In this preferred embodiment of the invention, the autoclave 11 comprises a pressure vessel 13 having a sterilization chamber 15 formed therein, and the sterilization chamber 15 has an interior 17 where steam treatment (e.g., sterilization) takes place. The pressure vessel 13 has a forging 19 thereon that forms an opening 21 through which access to the interior 17 of the sterilization chamber 15 is obtained.

The steam autoclave 11 also has a steam injection piping system that includes a first piping to supply steam from a steam source (e.g., a main steam line) to the sterilization chamber 15, and the steam injection piping system preferably also includes along the first piping a manual isolation valve (preferably a manual ball valve) as a safety feature, a steam pressure reducer for lowering the pressure level of the steam from the steam source (e.g., the main steam line that feeds the steam to the first piping) to a lower operating pressure (e.g., a pressure selected to use in the operation of the steam autoclave 11), and an automated control valve whose opening and closing during the steam treatment cycle of the steam autoclave 11 is set by selected pressure levels (selected pressure set points) for pressure in the sterilization chamber 15 of the steam autoclave 11. The steam autoclave 11 preferably also includes a second piping in communication with the sterilization chamber 15 through which steam may be evacuated from the sterilization chamber 15, a vacuum pump (when desired) provided along the second piping for evacuating the sterilization chamber 15 when desired during the treatment process, and a valve (preferably an electromagnetic solenoid activated valve) provided along a vent portion of the second piping used for venting the steam sterilization chamber to atmosphere. The steam autoclave 11 preferably also was provided with a condensate drainage system for draining condensate from the sterilization chamber 15. To simplify the drawings, standard component parts of steam autoclaves, such as the above-mentioned steam injection piping system, the second piping, vacuum pump, vent portion of the second piping, valve along the vent portion of the second piping, and the condensate drain system, are not shown. Preferably, the autoclave systems and the method of operation disclosed in Robert W. Lewis's U.S. Pat. Nos. 6,867,393 and 7,815,851, which are incorporated herein by reference, may be used in our invention, but with the modifications disclosed herein.

Figure 2:
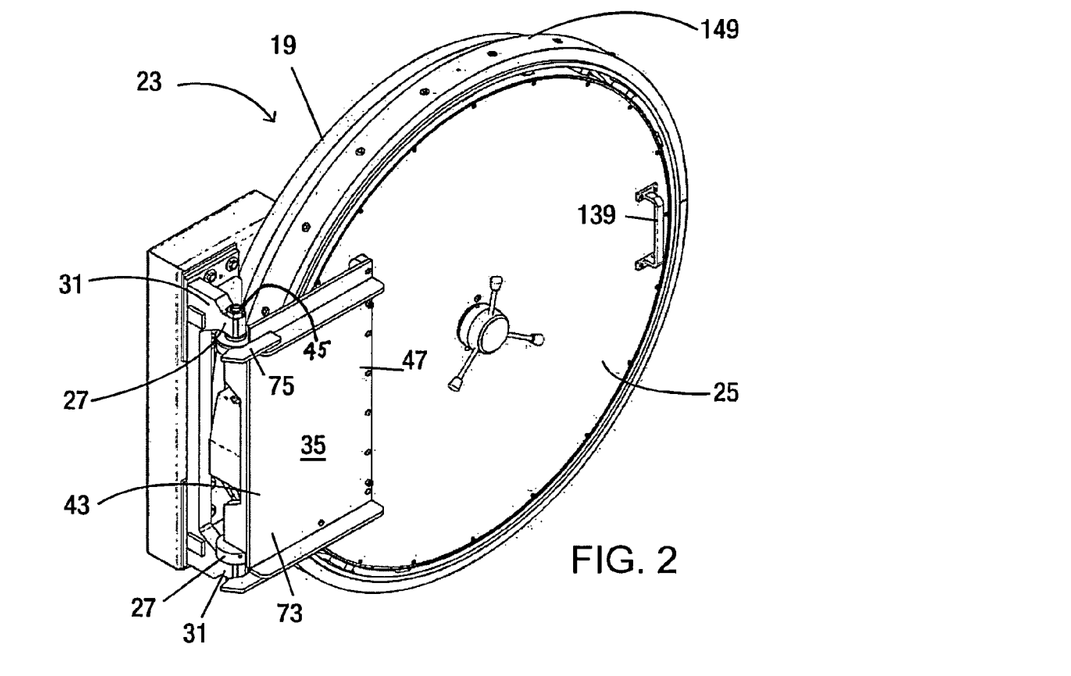
FIG. 2 is a view in perspective of an autoclave door apparatus 23 constructed in accordance with the invention.

A door apparatus 23 is provided and includes a door 25 for opening and closing the opening 21 to the interior 17 of the sterilization chamber 15.

Figure 3:
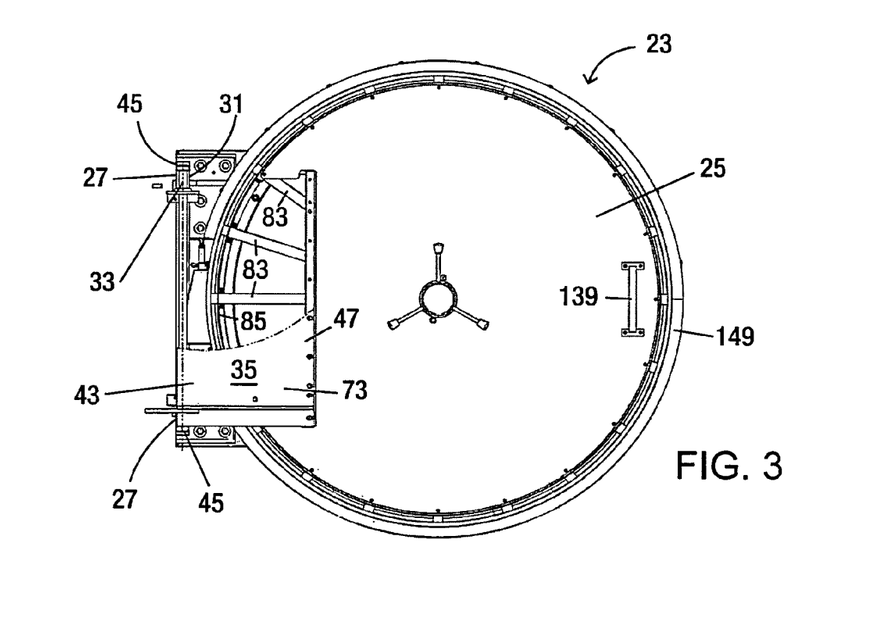
FIG. 3 is a view in front elevation of the door apparatus 23 shown in FIG. 2, with a cut-away showing details of the primary hinge assembly 27, various latch bars 83 extending through openings 87 in an alignment ring 85 and interacting with a latch ring 91 of the inventive door apparatus 23, and a portion of a locking mechanism 175 for locking the door 25 in a latched position.
Figure 4:
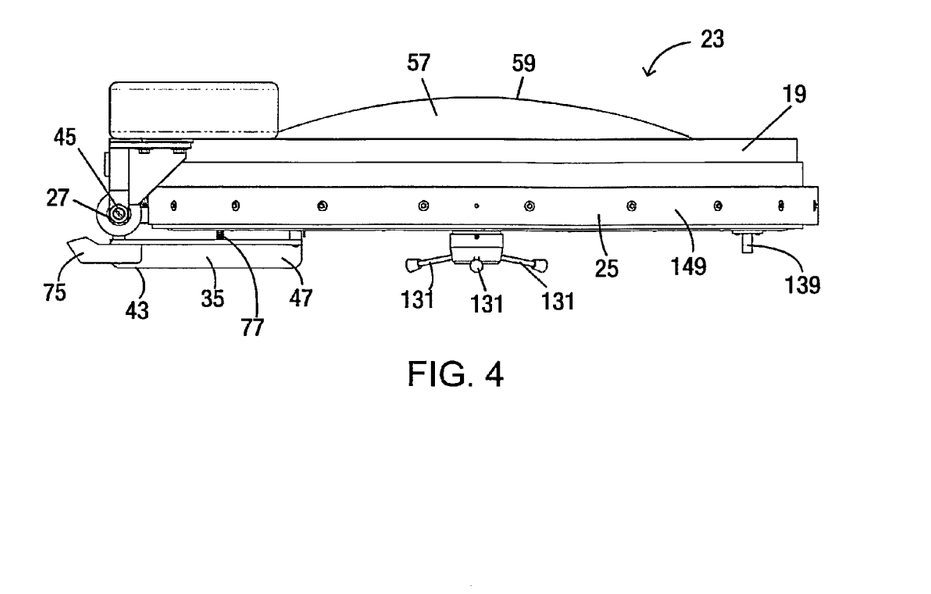
FIG. 4 is a top plan view of the door apparatus 23 shown in FIG. 2.
Figure 5:
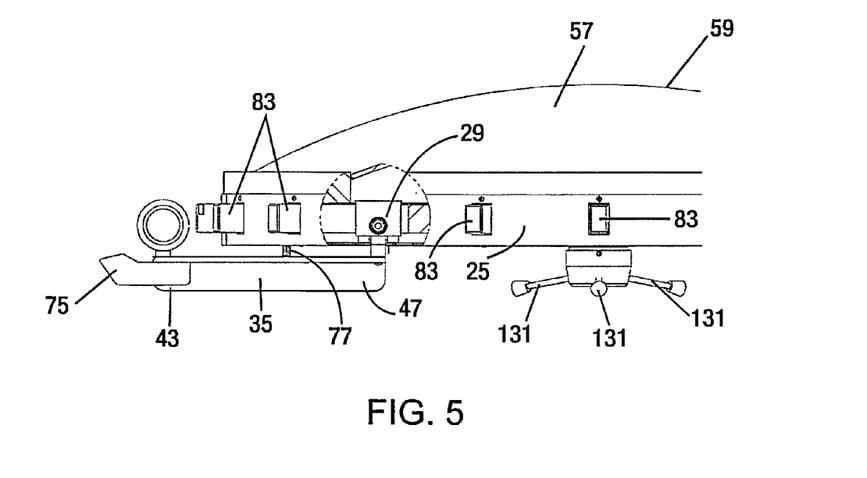
FIG. 5 is a partial top plan view of the door 25 constructed in accordance with the invention, with a cut-away showing a secondary hinge assembly 29.
Figure 7:
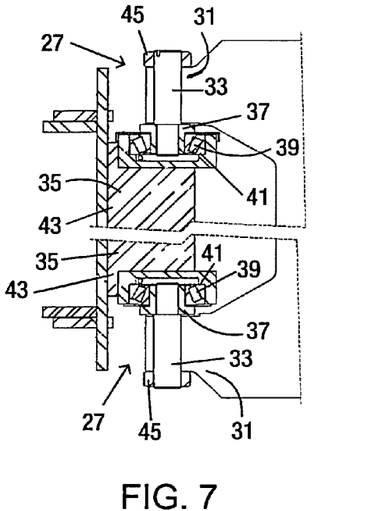
FIG. 7 is a view in cross-section illustrating the primary hinge assembly 27.
Figure 8:
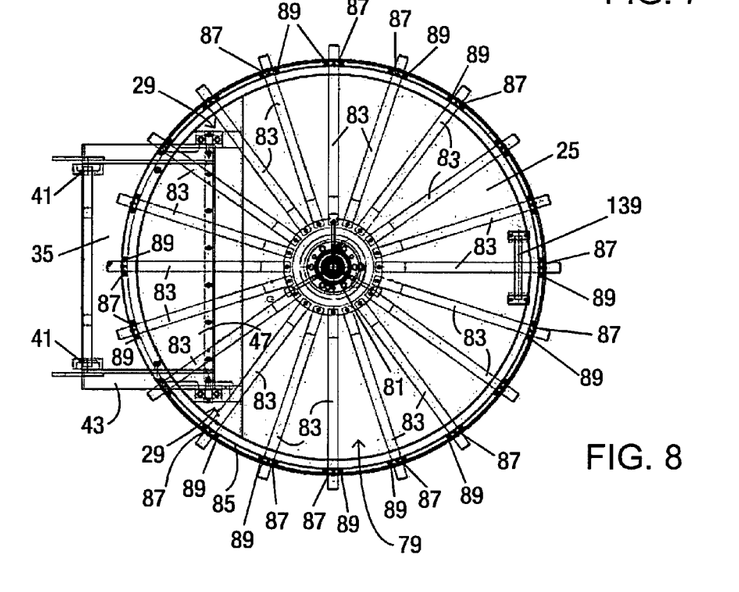
FIG. 8 is a view in front elevation of the door 25 (without its door skin 147 attached thereto) and the door mounting plate assembly 35 (without its cover plate 73 attached thereto).

Preferably, the door 25 is hingedly mounted on the pressure vessel 13. In a preferred embodiment of the invention, a primary hinge assembly 27 and a secondary hinge assembly 29 are provided. As shown in FIGS. 2-4, and in particular in FIG. 7, the primary hinge assembly 27 includes a pair of hinge brackets 31 extending outwardly from the pressure vessel 13, and each of the hinge brackets 31 has a bore extending through it, with the two bores being aligned with each other. A pair of hinge bearing axles 33 is used to connect a door mounting plate assembly 35 to the hinge brackets 31. At each hinge bracket 31, a hinge bearing axle 33, which has threaded end portions, is placed in the bore of the hinge bracket 31 such that a portion of each end of the hinge bearing axle 33 extends from the bore, with one end portion of the hinge bearing axle 33 being threaded into a hollow substantially cylinder-shaped loading mechanism (bushing) 37 having a tapered outer surface that rides on a bearing 39 secured in a recess 41 in a first end portion 43 of the door mounting plate assembly 35, and the other end portion of the hinge bearing axle 33 having hex nut 45 threaded thereon to hingedly mount the first end portion 43 of the door mounting plate assembly 35 onto the pressure vessel 13.

As shown in FIGS. 5, 8, 10, and 13, the secondary hinge assembly 29 connects the second end portion 47 of the door mounting plate assembly 35 to the door 25. In a fashion similar to the primary hinge assembly 27, the secondary hinge assembly 29 is provided with a pair of hinge brackets 49, but these hinge brackets 49 are connected by bolts 51 to mounting plates 53 welded to the inside surface 55 of a panel 57 that forms a portion of the first side 59 of the door 25, the first side 59 of the door 25 facing and extending across the opening 21 to the interior 17 of the sterilization chamber 15 when the door 25 is in a closed position. In a similar fashion to the primary hinge assembly 27, a pair of hinge axles 61 is used to connect the second end portion 47 of the door mounting plate assembly 35 to the hinge brackets 49. At each hinge bracket 49, a hinge axle 61, which has threaded end portions, is placed in the bore extending therethrough such that a portion of each end portion of the threaded hinge axle 61 extends from the bore, with one end portion of the hinge axle 61 being threaded into a hollow cylinder-shaped loading mechanism (bushing) 63 that rides on a washer 65, and the other end portion of the hinge axle 61 having a hex nut 71 threaded thereon, to hingedly mount the door 25 to the second end portion 47 of the door mounting plate assembly 35.

Preferably, the door mounting plate assembly 35 is provided with a skin or cover plate 73 that is bolted in place on the door mounting plate assembly 35. Also, preferably, a door stop 75 is provided on the first end portion 43 of the door mounting plate assembly 35 that engages the pressure vessel 13 when the door 25 is swung open up to a desired amount, thereby preventing the door 25 from being swung open beyond the desired amount.

Figure 6:
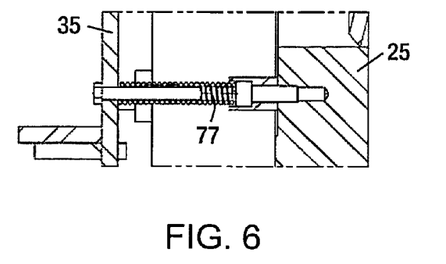
FIG. 6 is a view in partial cross-section showing a compression spring 77 mounted on and extending between the door 25 and a door mounting plate assembly 35 to prevent the door 25 from turning too far around the secondary hinge assembly 29.

Preferably, a compression spring 77 is mounted on and extends between the door 25 and the door mounting plate assembly 35 to prevent the door 25 from turning to far around the secondary hinge assembly 29.

Turning now to FIGS. 8-10, 12, and 14-16, preferably, the door 25 has a center spindle assembly 79 mounted thereon, and the center spindle assembly 79 includes a center spindle hub 81 rotatably mounted on the door 25 and a plurality of latch bars 83 hingedly mounted on the center spindle hub 81 and extending radially away from the center spindle hub 81. In order to maintain the latch bars 83 in proper alignment on the door 25, the door 25 preferably also has an alignment ring 85 mounted thereon which surrounds the center spindle hub 81. The alignment ring 85 has a plurality of openings 87 formed therein, and each latch bar 83 has a portion thereof that extends through and beyond a corresponding opening 87 from the plurality of openings 87 formed in the alignment ring 85. Preferably, a shim 89 is mounted on the alignment ring 85 at each opening 87 to assist in positioning the latch bar 83 in the correct position at the opening 87 in the alignment ring 85 that the latch bar 83 corresponds to to promote distribution of the forces on the door 25 created by the pressure generated in the sterilization chamber 15 during use evenly around the circumference of the door 25.

A latch ring 91 is mounted on the pressure vessel 13 (preferably positioned on or near the forging 19 of the pressure vessel 13) and surrounds the opening 21 to the interior 17 of the sterilization chamber 15. The latch ring 91 has a plurality of openings 93 formed therein, and each latch bar 83 has an end portion 95 that extends through and beyond a corresponding opening 93 from the plurality of openings 93 formed in the latch ring 91 when the door 25 is secured (latched) in a closed position (that is, in a position closing the opening 21 to the interior 17 of the sterilization chamber 15). As may be seen from the structure of the center spindle assembly 79 set out below, the center spindle hub 81 is operative when rotated around its axis in a first direction to cause the latch bars 83 to move outwardly such that their end portions 95 extend through and beyond the corresponding openings 93 in the latch ring 91 when the door 25 is in a closed position to secure (latch) the door 25 in the closed position, since the latch ring 91 engages and blocks the latch bars 83 from moving past the latch ring 91 if the door 25 is attempted to be opened when the end portions 95 of the latch bars 83 extend through and beyond the corresponding openings 93 in the latch ring 91 when the door 25 is in a closed position. The center spindle hub 81 also is operative when rotated around its axis in a direction opposite to the first direction to cause the latch bars 83 to move inwardly such that their end portions 95 no longer extend through and beyond the corresponding openings 93 in the latch ring 91 to permit the door 25 to be opened, since the latch ring 91 after the latch bars 83 have been moved inwardly such that their end portions 95 no longer extend through and beyond their corresponding openings 93 in the latch ring 91 no longer block the latch bars 31 when the door 83 is pulled to open it.

Figure 9:
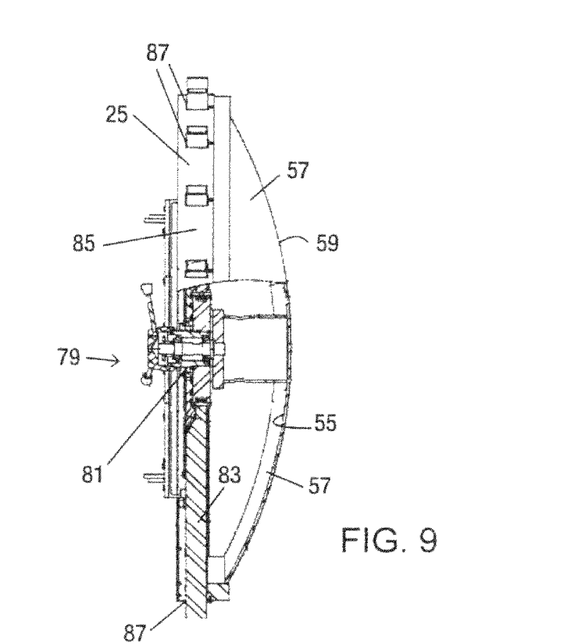
FIG. 9 is a side elevational view in partial cross-section of the door 25 of the invention.
Figure 10:
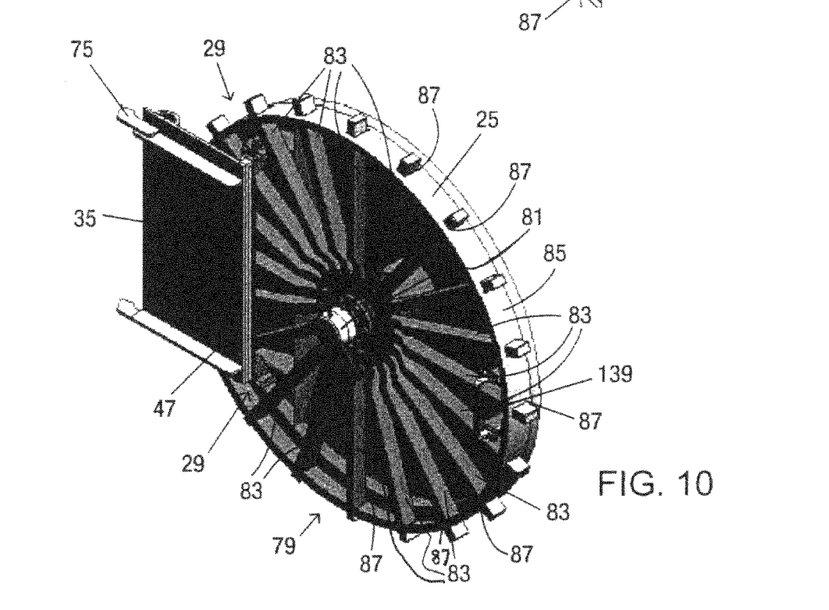
FIG. 10 is a view in perspective showing the door 25 (without its door skin 147 attached thereto) and the secondary hinge assembly 29 connecting the second end portion 47 of the door mounting plate assembly 35 to the door 25.
Figure 14:
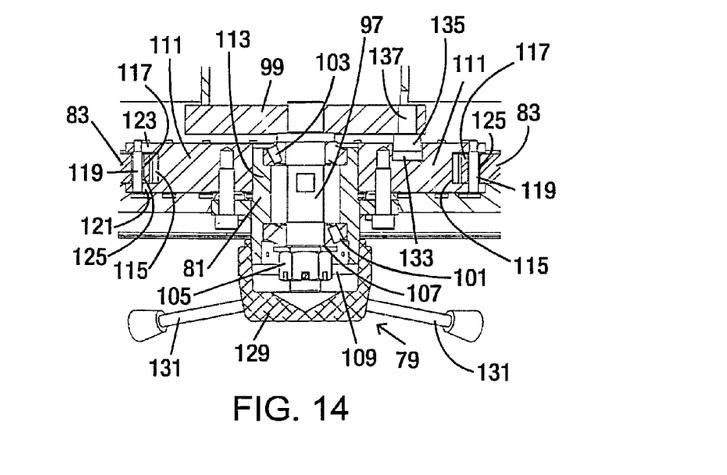
FIG. 14 is a partial view in cross-section of the center spindle assembly 79.
Figure 16:
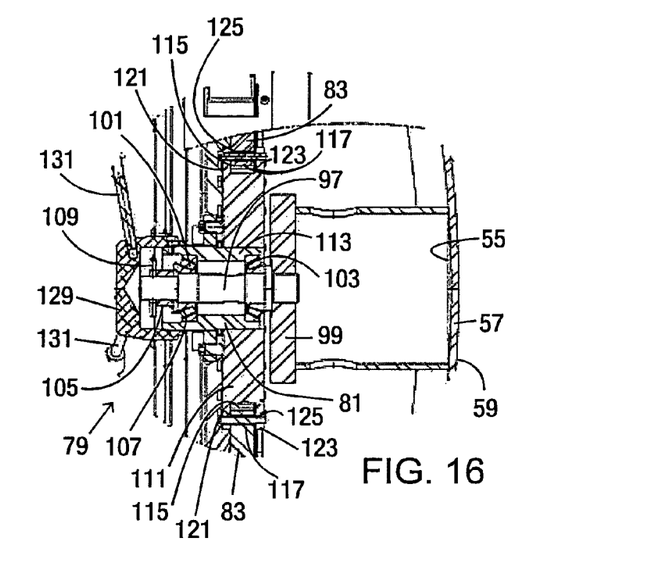
FIG. 16 is a partial view in cross-section showing the center spindle assembly 79.

In a preferred embodiment of the invention, as shown in the drawings at FIGS. 9, 14, and 16, the center spindle hub 81 is rotatably mounted around a center spindle shaft 97 that is fixedly mounted in place to a spindle weldment 99 (e.g., the center spindle shaft 97 is threaded into and glued or cemented in place in the spindle weldment 99) that is welded to the inside surface 55 of the panel 57 that forms a portion of the first side 59 of the door 25. The center spindle hub 81 rides on bearings 101 and 103 positioned between the center spindle shaft 97 and the center spindle hub 81. A locking adjustment nut 105 and washer 107 are provided on one end of the center spindle shaft 97 to hold the center spindle hub 81 in position over the center spindle shaft 97. A kotter pin 109 extends through the center spindle shaft 97 adjacent to the locking adjustment nut 105 to keep the locking adjustment nut 105 from inadvertently rotating outwardly off of the center spindle shaft 97.

The center spindle hub 81 includes an outwardly extending flange 111 formed by welding an annular cylindrical plate around a portion of the center tube-like section 113 of the center spindle hub 81. A groove 115 is formed in the side portion of the flange 111, and the groove 115 extends completely around the flange 111. The groove 115 is provided to receive the inner end portions 117 of the latch bars 83, which are secured in the groove 115 with bolts 119 that are secured to and extend between the opposing walls 121 and 123 formed in the flange 111 by the groove 115. Each bolt 119 extends through an opening 125 formed in the inner end portion 117 of a corresponding latch bar 83 to hingedly mount each of the latch bars 83 to the flange 111.

The center spindle hub 81 is provided with a cap 129 that is bolted to the center spindle hub 81, and the cap 129 has spindle hub handles 131 bolted thereto that may be grasped and pulled on to facilitate rotation of the center spindle hub 81.

The door 25 may be latched closed by using the spindle hub handles 131 to rotate the center spindle hub 81 in a first direction to cause the latch bars 83 to move outwardly such that their end portions 95 extend through and beyond the corresponding openings 93 in the latch ring 91 when the door 25 is in a closed position to secure (e.g., latch) the door 25 in the closed position. Likewise, the door 25 may be unlatched, when desired, by using the spindle hub handles 131 to rotate the center spindle hub 81 in a direction opposite to the first direction to cause the latch bars 83 to move inwardly such that their end portions 95 no longer extend through and beyond the corresponding openings 93 in the latch ring 91 when the door 25 is in a closed position to permit the door 25 to be opened.

Referring to FIG. 14, an arc-shaped groove 133 is formed in the portion of the flange 111 facing the spindle weldment 99, and the groove 133 receives a bolt head 135 of a bolt 137 attached to the spindle weldment 99. The length of the groove 133 defines the bounds that the center spindle hub 81 may be rotated since the bolt head 135 acts as a stop when it engages either end of the groove 133.

Figure 11:
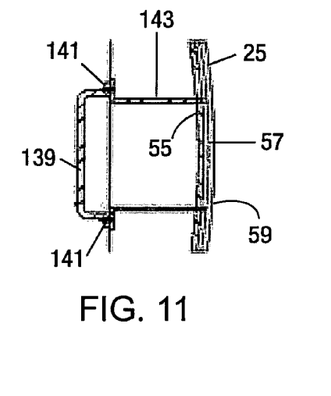
FIG. 11 is a view in cross-section showing the pull handle 139 mounted on a bracket 143 welded to the inside surface 55 of the panel 57 that forms a portion of the first side 59 of the door 25.
Figure 12:
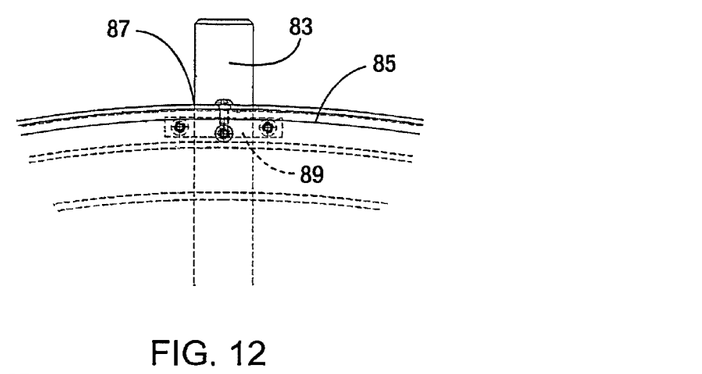
FIG. 12 is a partial view in elevation showing a portion of a latch bar 83 protruding through an opening 87 in the alignment ring 85.
Figure 13:
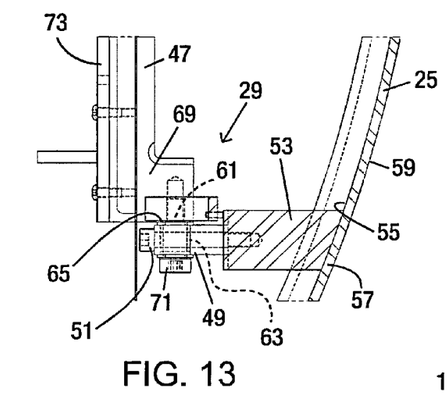
FIG. 13 is a partial view in cross-section showing a portion of the secondary hinge assembly 29.

A pull handle 139 (FIGS. 2-4, 8, 10, and 11) that may be grasped and pulled or pushed preferably is provided for facilitating moving the door 25 into opened and closed positions. As shown in FIG. 11, the pull handle 139 preferably is mounted on the door 25 using bolts 141 that attach the pull handle 139 to a bracket 143 that is welded to the inside surface 55 of the panel 57 that forms a portion of the first side 59 of the door 25.

Figure 15:
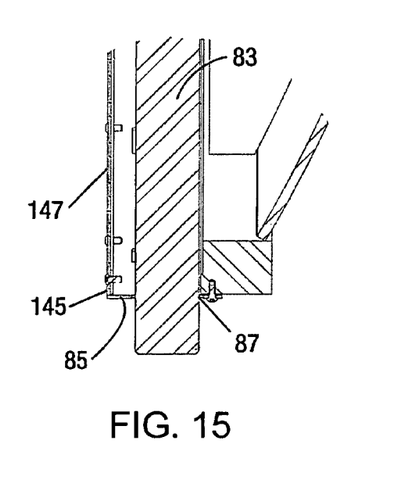
FIG. 15 is a partial view in cross-section of the door 25, showing a latch bar 83 protruding through an opening 87 in the alignment ring 85, and the door skin 147 mounted on the alignment ring 85.
Figure 19:
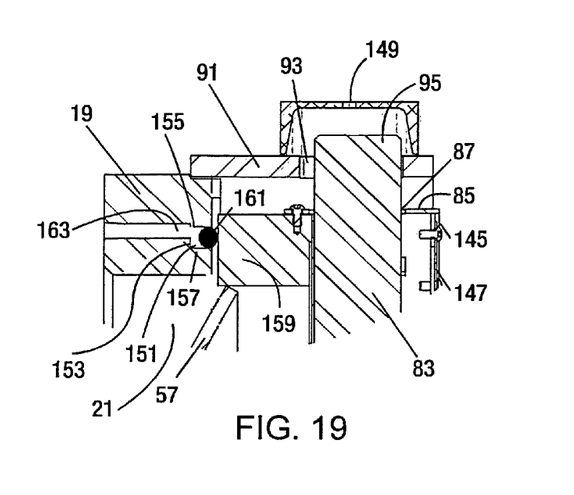
FIG. 19 is a partial view in cross-section, showing the pneumatic seal between the door 25 and the forging 19 of the pressure vessel 13 when the door 25 is in a closed and latched position.

As shown in FIGS. 15 and 19, the alignment ring 85 preferably has an annular flange 145 that extends radially inwardly towards the center axis of the alignment ring 85, and a door skin (e.g., a cover plate) 147 is attached (e.g., bolted) to it to cover the center spindle assembly 79 (except for the portions of the center spindle assembly 79, the portions of the secondary hinge assembly 29, and the bolts 141 that attach the pull handle 139 to the bracket 143, that extend through openings in the door skin 147).

As shown in FIG. 19, an annular safety cover 149 preferably is positioned around the circumference of the latching ring 91 covering the end portions 85 of the latching bars 83 when they extend through the openings 93 in the latch ring 91. The safety cover 149 provides sufficient space between the safety cover 149 and the latch ring 91 such that the safety cover 149 does not interfere with the latch bars 83.

As shown in FIG. 19, a groove 151 is formed in the forging 19. The groove 151 is defined by a back wall 153, and two side walls 155 and 157 that extend outwardly away from the back wall 153. The groove 151 surrounds the opening 21 to the interior 17 of the sterilization chamber 15, and the groove 151 faces towards a portion (e.g., the door forging 159) of the door 25 when the door 25 is in a closed position.

During use of the autoclave 11, a flexible sealing member 161, such as an o-ring made of silicone, is positioned in the groove 151, and is sized to be in contact with both side walls 155 and 157 of the groove 151 when the flexible sealing member 161 is in the groove 151.

At least one port 163 is provided in the groove 151 through which compressed gas, preferably compressed air, may be introduced into the groove 151 between the flexible sealing member 161 and the back wall 153 of the groove 151, but preferably a plurality of such ports 163 is provided, preferably with ports 163 being equally spaced from each other along the groove 151.

The flexible sealing member 161 is operative to seal between the forging 19 of the pressure vessel 13 and the door 25 (preferably, along the door forging 159 as shown in the drawings) when compressed gas (preferably compressed air) is introduced through the at least one port 163 (or ports 163 if there is more than one port 163 provided) when the door 25 is secured in a closed position closing the opening 21 to the interior 17 of the sterilization chamber 15 to push the flexible sealing member 161 partially from the groove 151 into sealing contact with the door 25 (e.g., the door forging 159 as shown in the drawings), thereby creating a pneumatic seal between the door 25 and the forging 19.

Preferably, the panel 57 that forms the first side 59 of the door 25 has a convex shape that extends into the opening 21 to the interior 17 of the sterilization chamber 15. The concave shape of the panel 57 aids in providing an even distribution of steam throughout the sterilization chamber 15 since steam hitting it ricochets off of the convex surface of the panel 57 generally in a greater number of directions, when compared with a flat door, thus distributing the steam that hits it during a steam treatment more evenly throughout the sterilization chamber 15.

Figure 20:
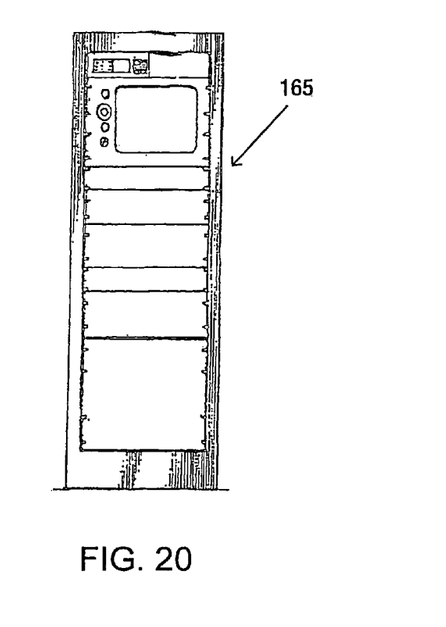
FIG. 20 is a view in front elevation showing control means (e.g., a programmable logic controller) 165 for the autoclave 11.

Preferably, control means (e.g., a computer, or a controller (preferably, a programmable logic controller)) 165 is connected to the autoclave 11 for managing the control functions of the autoclave 11. The control means 165 controls the steam valves, vent valves, drain valves, and vacuum pump. The control means 165 also is provided for monitoring and recording process temperatures and pressures that occur during the process of treating objects and materials, such as medical waste, in the autoclave 11, for activating and deactivating introduction of compressed gas through the at least one port 163 or ports 163 into the groove 151 between flexible sealing member 161 and the back wall 153 of the groove 151, for monitoring gas pressure in the groove 151 between the flexible sealing member 161 and the back wall 153 of the groove 151, for initiating a vacuum to be drawn in the sterilization chamber 15 upon completing treatment of the materials to be treated (e.g., medical waste) in the sterilization chamber 15 to draw the door 25 inwardly to push the flexible sealing member 161 back towards the back wall 153 of the groove 151 when it is time to reseat the flexible sealing member 161 in the groove 151, and for activating and deactivating locking means 167 (discussed below) for locking the door 25 in a latched position and for unlocking the door 25. Also, the control means 165 is connected to a switch mechanism 169 (discussed below) that operates to communicate to the control means 165 when the door 25 is in a closed and latched position.

The switch mechanism 169 (FIGS. 17 and 18) preferably is operatively connected to the control means 165 for indicating to the control means 165 when the door 25 is in a closed and latched position. Preferably, the switch mechanism 169 includes an activation lever 171, which has a roller 173 mounted on its free end. By pushing on the roller 173 with the end of a latch bar 83 as the door 25 is being latched when the door 25 is in a closed position, the activation lever 171 may be pushed from a first position into a second position when the door 25 is in a closed and latched position. When the activation lever 171 is pushed into the second position by the latch bar 83, it activates the switch mechanism 169 to initiate a signal from the switch mechanism 169 to the control means 165 indicating to the control means 165 that the door 25 is in a closed and latched position.

Figure 17:
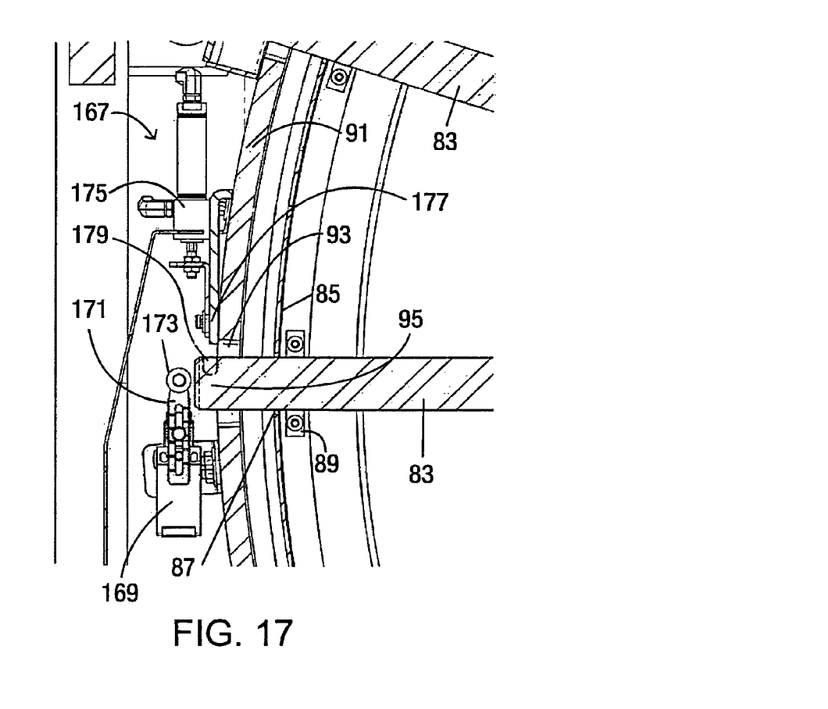
FIG. 17 is a partial view in partial cross-section showing a switch mechanism 169 and an activation lever 171 which are used to indicate to the control means 165 when the door 25 is in a closed and latched position, and showing locking means 167 for locking the door 25 in a closed and latched position.
Figure 18:
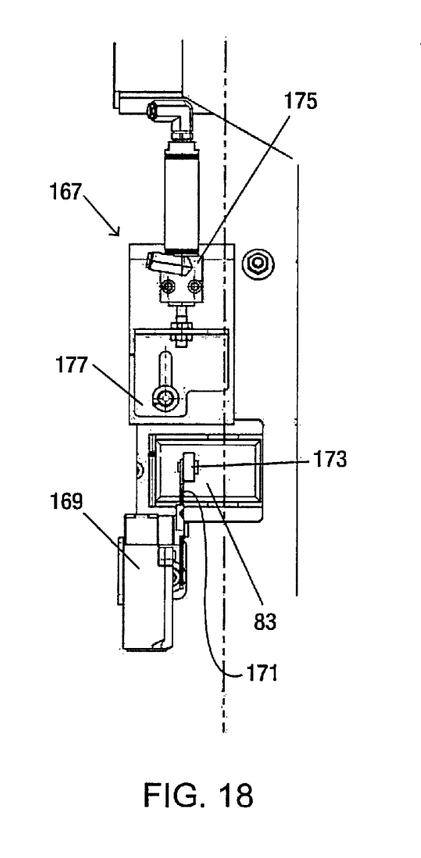
FIG. 18 is a partial view in elevation showing a switch mechanism 169 and an activation lever 171 which are used to indicate to the control means 165 when the door 25 is in a closed and latched position, and showing locking means 167 for locking the door 25 in a closed and latched position.

Preferably, the locking means 167 for locking one of the latch bars 83 in place after the door 25 has been latched (that is, after the center spindle hub 81 has been rotated around its axis to cause the latch bars 83 to move radially outwardly such that their end portions 95 extend through the corresponding openings 93 in the latch ring 91 when the door 25 is in a closed position, thereby preventing the center spindle hub 81 from being rotated back around its axis to cause the latch bars 83 to move radially inwardly such that their end portions 95 no longer extend through the corresponding openings 93 in the latch bar 91) to prevent the door 25 from opening when the sterilization chamber 15 is pressurized. Preferably, the locking means 167 comprises a locking mechanism 175 that preferably is an electric or pneumatic device that extends, when desired, a blocking member 177 (e.g., a plate such as that shown in the drawings, or a rod) into an opening 179 (e.g., a slot, groove, or hole) formed in one of the latch bars 83 when the door 25 is in a closed and latched position (that is, when the door 25 is in a position closing the opening 21 to the interior 17 of the sterilization chamber 15 and the latch bars 83 have been moved radially outwardly by rotating the center spindle hub 81 in a first direction such that the end portions 95 of the latch bars 83 extend through the corresponding openings 93 in the latch ring 91) to block the latch bar 83 that has the blocking member 177 extending into the opening 179 in the latch bar 83 from moving radially inwardly, thereby preventing the center spindle hub 81 from rotating in a direction opposite the first direction while the blocking member 177 extends into the opening 179 in the latch bar 83, thereby preventing all the latch bars 83 from moving radially inwardly such that their end portions 95 no longer extend through the corresponding openings 93 in the latch ring 91. The control means 165, which is connected to the locking means 167, sends a signal to the locking mechanism 175 to trigger the locking mechanism 175 to extend the blocking member 177 into the opening 179 formed in one of the latch bars 83 when the door 25 is in a closed and latched position to lock the door 25 in a closed and latched position, and sends a signal to the locking mechanism 175 to trigger the locking mechanism 175 to retract the blocking member 177 from the latch bar 83 when it is desired to unlock the door 25 from a latched position.

Preferably, a sensor (not shown) is provided preferably in the groove 151 or in the conduit connecting the grove 151 to the compressed gas source to monitor the pressure level of the compressed gas held between the back wall 153 of the groove 151 and the flexible sealing member 161. The sensor is connected to the control means 165, which triggers a pressure regulator in the pressure line feeding the port 163 or ports 163 with compressed gas to regulate the amount of compressed gas feed into the groove 151 so that a sufficient pneumatic seal is achieved to seal between the forging 19 and the door 25 when a steam treatment is taking place within the sterilization chamber 15.

In use, the door 25 operates as follows. Starting with the door 25 in an open position (that is, the door 25 swung away from the opening 21 to the interior 17 of the sterilization chamber 15), the material (e.g., medical waste) to be treated in the sterilization chamber 15 may be position inside the sterilization chamber 15. After the sterilization chamber 15 has been loaded with the material to be treated by the autoclave 11, the door 25 may be swung into a closed position by grasping onto the handle 139 and pushing against it until the door 25 closes off the opening 21 to the interior 17 of the sterilization chamber 15. The door 25 is then latched shut by using the handles 131 to rotate the center spindle hub 81 in a first direction to cause the latch bars 83 to move radially outwardly so that their end portions 95 extend through and beyond the corresponding openings 93 in the latch ring 91.

When the door 25 is in this closed and latched position, the activation lever 171 has been moved into a second position by one of the latch bars 83 abutting against and pushing the roller 173 mounted on the activation lever 171 as the latch bar 83 moves radially outwardly due to the rotation of the center spindle hub 81, which triggers the switch mechanism 169 to send a signal to the control means 165 indicating that the door 25 has been placed in a closed and latched position. In response to this signal from the switch mechanism 169, the control means 165 sends a signal to the locking means 167 to trigger the locking mechanism 175 to extend (which for illustrative purposes shown in the drawings may be done using a pneumatic cylinder) the blocking member 177 (e.g., a plate attached to the pneumatic cylinder as shown for illustrative purposes in the drawings) into the opening 179 (e.g., a slot as shown for illustrative purposes in the drawings) in one of the latch bars 83 to lock the door 25 in the closed and latched position to prevent the door 25 from opening when the sterilization chamber 15 is to be pressurized or is pressurized. After the door 25 has been locked in a closed and latched position, the control means 165 sends a signal to a compressed gas source to initiate the introduction of compressed gas from the compressed gas source to the grove 151 via a conduit connecting the compressed gas source to the at least one port 163, or to the ports 163 if more than one port 163 is provided in the groove 151, so that compressed gas may fill the space between the back wall 153 of the groove 151 and the flexible sealing member 161. Sufficient compressed gas is feed into the groove 151 to cause the flexible sealing member 161 to project partially from the groove 151 into sealing contact with the door 25 (e.g., into sealing contact with the door forging 159 of the door 25) to create a pneumatic seal to seal between the door 25 and the forging 19 of the pressure vessel 13, thereby sealing closing the door 25 over the opening 21 to the interior 17 of the sterilization chamber 15 so that treatment of the material (e.g., medical waste) placed in the sterilization chamber 15 may begin.

After treatment of the material (e.g., medical waste) placed in the sterilization chamber 15 has been completed, the door 25 may be opened as follows to permit the material (e.g., medical waste) that has been treated in the sterilization chamber 15 to be removed from the sterilization chamber 15. First, the pressure in the groove 151 is removed and vacuum is drawn in the sterilization chamber 15 to pull the door 25 inwardly against the forging 19 of the pressure vessel 13, resulting in the flexible sealing member 161 being pressed back into the groove 151 by the door forging 159 to reset the flexible sealing member 161 to its original position in the groove 151 prior to it being pushed partially therefrom to create the pneumatic seal between the pressure vessel forging 19 and the door forging 159 when the groove 151 was filled with compressed gas. Alternatively, vacuum may be drawn in the groove 151 via the conduit leading to the port 163 or ports 163 to pull the flexible sealing member 161 back towards the back wall 153 of the groove 151. The control means 165 then releases the vacuum in the sterilization chamber 15, and then sends a signal to the locking mechanism 175 to trigger the locking mechanism 175 to retract the blocking member 177 so that it no longer extends into the opening 179 of the latch bar 83 to unlock the door 25. With the door 25 unlocked, the center spindle hub 81 may be rotated using the handles 131 to cause the latch bars 83 to move radially inwardly so that the end portions 95 of the latch bars 83 no longer extend through the corresponding openings 93 in the latch ring 91, thereby unlatching the door 25. The door 25 then may be swung open by pulling on the handle 139. When the latch bars 83 are moved radially inwardly during the unlatching of the door 25, the activation lever 171 moves back into its first position, the activation lever 171 being biased toward the first position by a spring.

ADVANTAGES

The advantages of the invention over previously employed methods and apparatus include the following:

(1) The convex-shaped panel 57 aids in the even distribution of steam into the autoclave chamber 15.

(2) Our invention provides a pneumatic seal, which eliminates reliance on the autoclave operator to tighten the autoclave door sufficiently since our invention maintains the optimum seal pressure automatically throughout the autoclave process treatment.

(3) Pneumatic operation of the seal avoids problems of hydraulic systems and their potential for leaks of hydraulic fluids into the environment, as well as avoiding the problems with pressure wedges which wear and are difficult to renew.

(4) Our invention allows for an easy manual swinging operation of the door 25.

(5) Our invention allows for easy latching of the door 25 in the closed position and for easy unlatching of the door 15 to permit it to be opened.

(6) Our invention provides a positive locking of the door 25 when it is in the closed position.

(7) The process of drawing vacuum in the pressure vessel 13 to unseal the door 25 and reseat the flexible sealing member 161 aids in the reduction of the release of odors and steam form the door 25 upon opening of the door 25.

What is claimed is:
1. An autoclave for treating medical waste, comprising
a pressure vessel having a sterilization chamber therein, the sterilization chamber having an interior, the pressure vessel having a forging thereon that forms an opening through which access to the interior of the sterilization chamber is obtained,
a door for opening and closing the opening,
the door having a center spindle assembly mounted thereon,
the center spindle assembly including a center spindle hub rotatably mounted on the door and a plurality of latch bars hingedly mounted on the center spindle hub and extending radially away from the center spindle hub,
the door having an alignment ring mounted thereon surrounding the center spindle hub, the alignment ring having a plurality of openings formed therein, each latch bar having a portion thereof extending through a corresponding opening from the plurality of openings formed in the alignment ring,
a latch ring positioned on the forging, the latch ring surrounding the opening to the interior of the sterilization chamber, the latch ring having a plurality of openings formed therein, each latch bar having a portion thereof extending through a corresponding opening from the plurality of openings formed in the latch ring when the door is secured in a closed position,
the center spindle hub being operative when rotated around its axis in a first direction to cause the latch bars to move outwardly such that their end portions extend through the corresponding openings in the latch ring when the door is in a closed position to secure the door in the closed position, and the center spindle hub being operative when rotated around its axis in a direction opposite to the first direction to cause the latch bars to move inwardly such that their end portions no longer extend through the corresponding openings in the latch ring to permit the door to be opened, a groove formed in the forging, the groove having a back wall and two side walls extending outwardly away from the back wall, a flexible sealing member positioned in the groove, the flexible sealing member contacting the two side walls of the groove when the flexible sealing member is in the groove, and at least one port positioned in the groove through which compressed gas may be introduced into the groove between the flexible sealing member and the back wall of the groove, the flexible sealing member being operative to seal between the forging and the door when compressed gas is introduced through the at least one port when the door is secured in a closed position to push the flexible sealing member partially from the groove into sealing contact with the door, thereby creating a pneumatic seal to seal between the door and the forging.

2. The autoclave of claim 1, the door having a first side that faces and extends across the opening to the interior of the sterilization chamber when the door is in a closed position, and the first side of the door having a convex portion that extends into the opening to the interior of the sterilization chamber when the door is in a closed position.

3. The autoclave of claim 1, further including a switch mechanism operatively connected to a controller for indicating to the controller when the door is in a closed and latched position, the switch mechanism including an activation lever which may be pushed from a first position by a latch bar as the door is being latched when the door is in a closed position into a second position where the door is in a closed and latched position, the activation lever activating the switch mechanism when the activation lever reaches the second position to initiate a signal from the switch mechanism to the controller indicating that the door is in a closed and latched position.

4. The autoclave of claim 1, further including control means for activating and deactivating introduction of compressed gas through the at least one port into the groove between flexible sealing member and the back wall of the groove, for monitoring gas pressure in the groove between the flexible sealing member and the back wall of the groove, and for initiating a vacuum to be drawn in the sterilization chamber upon completing treatment of medical waste in the sterilization chamber to draw the door inwardly to push the flexible sealing member back towards the back wall of the groove when it is time to reseat the flexible sealing member in the groove.

5. The autoclave of claim 1, the center spindle assembly including a handle mounted thereon, the handle being operative to rotate the center hub axially.

6. The autoclave of claim 1, further including a handle mounted on the door to facilitate opening and closing the door.

7. An autoclave for treating medical waste, comprising a pressure vessel having a sterilization chamber therein, the sterilization chamber having an interior, the pressure vessel having a forging thereon that forms an opening through which access to the interior of the sterilization chamber is obtained, a door for opening and closing the opening, the door having a center spindle assembly mounted thereon, the center spindle assembly including a center spindle hub rotatably mounted on the door and a plurality of latch bars hingedly mounted on the center spindle hub and extending radially away from the center spindle hub, the door having an alignment ring mounted thereon surrounding the center spindle hub, the alignment ring having a plurality of openings formed therein, each latch bar having a portion thereof extending through a corresponding opening from the plurality of openings formed in the alignment ring, a latch ring positioned on the forging, the latch ring surrounding the opening to the interior of the sterilization chamber, the latch ring having a plurality of openings formed therein, each latch bar having a portion thereof extending through a corresponding opening from the plurality of openings formed in the latch ring when the door is secured in a closed position, the center spindle hub being operative when rotated around its axis in a first direction to cause the latch bars to move outwardly such that their end portions extend through the corresponding openings in the latch ring when the door is in a closed position to secure the door in the closed position, and the center spindle hub being operative when rotated around its axis in a direction opposite to the first direction to cause the latch bars to move inwardly such that their end portions no longer extend through the corresponding openings in the latch ring to permit the door to be opened, a groove formed in the forging, the groove having a back wall and two side walls extending outwardly away from the back wall, a flexible sealing member positioned in the groove, the flexible sealing member being in contact with the two side walls of the groove when the flexible sealing member is in the groove, and at least one port positioned in the groove through which compressed gas may be introduced into the groove between the flexible sealing member and the back wall of the groove, the flexible sealing member being operative to seal between the forging and the door when compressed gas is introduced through the at least one port when the door is secured in a closed position to push the flexible sealing member partially from the groove into sealing contact with the door, thereby creating a pneumatic seal to seal between the door and the forging and further including locking means for locking one of the latch bars in place after the center spindle hub has been rotated around its axis to cause the latch bars to move outwardly such that their end portions extend through the corresponding openings in the latch ring when the door is in a closed position, thereby preventing the center spindle hub from being rotated back around its axis to cause the latch bars to move inwardly such that their end portions no longer extend through the corresponding openings in the latch bar.

8. The autoclave of claim 7, the locking means including a locking mechanism having a blocking member that is extendable therefrom, and an opening in one of the latch bars into which the blocking member may be extended when said one of the latching bars has its end portion extending through a corresponding opening in the latch ring when the door is in a closed position.

9. The autoclave of claim 7, further including
control means connected to the locking means for activating and deactivating the locking means.

10. An autoclave door apparatus for an autoclave for treating medical waste, comprising
a forging that forms an opening into and from an autoclave,
a door for opening and closing the opening into and from the autoclave,
the door having a center spindle assembly mounted thereon,
the center spindle assembly including a center spindle hub rotatably mounted on the door and a plurality of latch bars hingedly mounted on the center spindle hub and extending radially away from the center spindle hub,
the door having an alignment ring mounted thereon surrounding the center spindle hub, the alignment ring having a plurality of openings formed therein, each latch bar having a portion thereof extending through a corresponding opening from the plurality of openings formed in the alignment ring,
a latch ring positioned on the forging, the latch ring surrounding the opening into and from the autoclave, the latch ring having a plurality of openings formed therein, each latch bar having a portion thereof extending through a corresponding opening from the plurality of openings formed in the latch ring when the door is secured in a closed position,
the center spindle hub being operative when rotated around its axis in a first direction to cause the latch bars to move outwardly such that their end portions extend through the corresponding openings in the latch ring when the door is in a closed position to secure the door in the closed position, and the center spindle hub being operative when rotated around its axis in a direction opposite to the first direction to cause the latch bars to move inwardly such that their end portions no longer extend through the corresponding openings in the latch ring to permit the door to be opened,
a groove formed in the forging, the groove having a back wall and two side walls extending outwardly away from the back wall,
a flexible sealing member which is positioned in the groove during use,
the flexible sealing member contacting the two side walls of the groove when the flexible sealing member is in the groove, and
at least one port positioned in the groove through which compressed gas may be introduced into the groove between the flexible sealing member and the back wall of the groove,
the flexible sealing member being operative to seal between the forging and the door when compressed gas is introduced through the at least one port when the door is secured in a closed position to push the flexible sealing member partially from the groove into sealing contact with the door, thereby creating a pneumatic seal to seal between the door and the forging.

11. The door apparatus of claim 10,
the door being hingedly mounted on the autoclave when in use.

12. The door apparatus of claim 10,
the door having a first side that faces and extends across the opening into and from the autoclave when the door is in a closed position, and
the first side of the door having a convex portion that extends into the opening into and from the autoclave when the door is in a closed position.

13. The door apparatus of claim 10, further including
a switch mechanism operatively connected to a controller for indicating to the controller when the door is in a closed and latched position,
the switch mechanism including an activation lever which may be pushed from a first position by a latch bar as the door is being latched when the door is in a closed position, into a second position where the door is in a closed and latched position, the activation lever activating the switch mechanism when the activation lever reaches the second position to initiate a signal from the switch mechanism to the controller indicating that the door is in a closed and latched position.

14. The door apparatus of claim 10,
the center spindle assembly including a handle mounted thereon, the handle being operative to rotate the center hub axially.

15. The door assembly of claim 10, further including
a handle mounted on the door to facilitate opening and closing the door.

16. An autoclave door apparatus for an autoclave for treating medical waste, comprising
a forging that forms an opening into and from an autoclave,
a door for opening and closing the opening into and from the autoclave,
the door having a center spindle assembly mounted thereon,
the center spindle assembly including a center spindle hub rotatably mounted on the door and a plurality of latch bars hingedly mounted on the center spindle hub and extending radially away from the center spindle hub,
the door having an alignment ring mounted thereon surrounding the center spindle hub, the alignment ring having a plurality of openings formed therein, each latch bar having a portion thereof extending through a corresponding opening from the plurality of openings formed in the alignment ring,
a latch ring positioned on the forging, the latch ring surrounding the opening into and from the autoclave, the latch ring having a plurality of openings formed therein, each latch bar having a portion thereof extending through a corresponding opening from the plurality of openings formed in the latch ring when the door is secured in a closed position,
the center spindle hub being operative when rotated around its axis in a first direction to cause the latch bars to move outwardly such that their end portions extend through the corresponding openings in the latch ring when the door is in a closed position to secure the door in the closed position, and the center spindle hub being operative when rotated around its axis in a direction opposite to the first direction to cause the latch bars to move inwardly such that their end portions no longer extend through the corresponding openings in the latch ring to permit the door to be opened,
a groove formed in the forging, the groove having a back wall and two side walls extending outwardly away from the back wall,
a flexible sealing member which is positioned in the groove during use,
the flexible sealing member being in contact with the two side walls of the groove when the flexible sealing member is in the groove, and at least one port positioned in the groove through which compressed gas may be introduced into the groove between the flexible sealing member and the back wall of the groove, the flexible sealing member being operative to seal between the forging and the door when compressed gas is introduced through the at least one port when the door is secured in a closed position to push the flexible sealing member partially from the groove into sealing contact with the door, thereby creating a pneumatic seal to seal between the door and the forging and further including locking means for locking one of the latch bars in place after the center spindle hub has been rotated around its axis to cause the latch bars to move outwardly such that their end portions extend through the corresponding openings in the latch ring when the door is in a closed position, thereby preventing the center spindle hub from being rotated back around its axis to cause the latch bars to move inwardly such that their end portions no longer extend through the corresponding openings in the latch bar.

17. The door apparatus of claim 16, the locking means including the locking means including a locking mechanism having a blocking member that is extendable therefrom, and an opening in one of the latch bars into which the blocking member may be extended when said one of the latching bars has its end portion extending through a corresponding opening in the latch ring when the door is in a closed position.

* * * * *